United States Patent [19]

Schultz

[11] 4,154,969
[45] May 15, 1979

[54] PRODUCTION OF DIHYDROXYDIPHENYL ALKANES

[75] Inventor: Robert G. Schultz, St. Louis, Mo.

[73] Assignee: Monsanto Company, St. Louis, Mo.

[21] Appl. No.: 780,739

[22] Filed: Mar. 24, 1977

[51] Int. Cl.$^2$ .................. C07C 39/16; C07C 37/00
[52] U.S. Cl. ................................................ 568/729
[58] Field of Search .................. 260/619 B, 624 C; 568/729

[56] References Cited

U.S. PATENT DOCUMENTS 2,134,711  11/1938  Flett ........................... 260/624 C

OTHER PUBLICATIONS

Nosalevich et al., "Vestn. Khar'kov. Politekh. Inst.", (Ukrain), No. 60, (1971), pp. 61-64.

Primary Examiner—Joseph E. Evans
Attorney, Agent, or Firm—James C. Bolding

[57] ABSTRACT

A combination of zinc oxide and zinc bromide employed as a catalyst for the reaction between phenol and a 1,2-dihaloethane wherein the halogen is chlorine, bromine or iodine provides for increased reaction rates as compared to the use of either zinc compound separately as catalyst and elimination of the induction period characteristic of the reaction when zinc oxide is used as the catalyst.

4 Claims, No Drawings

PRODUCTION OF DIHYDROXYDIPHENYL ALKANES

BACKGROUND OF THE INVENTION

The present invention relates to the preparation of dihydroxydiphenyl alkanes by the reaction of phenol and dihaloakanes. More particularly, it relates to an improved catalyst for the preparation of 4,4'-dihydroxydiphenylethane sometimes referred to as bisphenol E.

Dihydroxydiphenyl alkanes, also known as bisphenols, are useful in the production of high polymers, epoxy resins and high-molecular weight thermoplastic condensates as well as intermediates in organic syntheses, the best known of such compounds, bisphenol A, being widely employed. It has been suggested in an article by I. M. Nosalevich et al entitled "Preparation of dihydroxydiphenylalkanes by the alkylation of phenol by dihaloalkanes" [Vestn. Khar'kov. Politekh. Inst. 1971, No 60, 61–4 (Ukrain)] that an increase in the number of technically available dihydroxydiphenyl alkanes would open up possibilities for modification of polymeric materials formed from them. Following this line, these workers have described several methods of preparing dihydroxydiphenyl alkanes among which is that of the direct interaction of phenol with dichloroethane or dibromoethane in the presence of zinc to give the 1,2-bis(4-hydroxyphenyl) ethane (also known as 4,4'-dihydroxydiphenylethane) and its isomers. Zinc-containing compounds such as the salts of zinc and particularly the halides of this metal as well as zinc oxide have been found to catalyze the reaction. It has now been discovered, however, that a combination of certain zinc-containing compounds is a more effective catalyst for this reaction and provides advantages which cannot be achieved with either of the zinc compounds used separately. It is an object of the present invention, therefore, to provide an improved catalytic process for the production of dihydroxydiphenyl alkanes using zinc-containing catalysts. It is a further object of this invention to provide a process for producing dihydroxydiphenyl alkanes from phenol and a dihaloethane wherein reaction rates are increased and the induction period observed with catalysts such as ZnO for example, is substantially eliminated. Further objects and advantages of the invention will become apparent from the following description and the appended claims.

SUMMARY OF THE INVENTION

According to the invention, phenol is alkylated with a 1,2-dihaloethane in which the halogen is chlorine, bromine or iodine in at least the stoichiometric proportions of 2:1 in contact with a catalyst comprising a combination of zinc oxide and zinc bromide in molar proportions in the range from about 1:10 to 10:1 at a temperature from about 125° to about 225° C. to produce 4,4'-dihydroxydiphenylethane.

DESCRIPTION OF THE PREFERRED EMBODIMENTS

The process of the invention is conveniently carried out in any apparatus of the type suitable for carrying out chemical reactions in the liquid phase using a solid catalyst, i.e., in a slurry-type reactor, or the liquid reactants can be pumped through a fixed bed of the catalyst. The reaction may be conducted as a batch or continuous operation.

Reactant mole ratios of the phenol to dihaloethane employed may vary from the stoichiometric ratio of 2:1 to as high as 10:1. Preferably, however, phenol-dihaloethane mole ratios in the range from 2:1 to 4:1 are employed.

The two components of the catalyst in the desired proportions are introduced into the reactor containing molten phenol separately as individual compounds either sequentially or simultaneously or they can be premixed and the mixture introduced into the reactor. No advantage is attained by dry mixing the components, however. The catalyst should be added to the reactor prior to heating to 100° C. Molar proportions of zinc oxide to zinc bromide may vary from 1:10 to 10:1 but preferably are in the range from 1:1 to 8:1.

The amount of catalyst employed generally may vary from about 0.001 to about 2 moles per mole of dihaloethane; preferably, an amount from about 0.01 to about 1 mole per mole of the dihaloethane reactant is employed.

The temperature at which the reaction proceeds varies in general from about 125° to about 225° C. depending upon the particular dihaloethane being reacted. The lower temperatures in the range, e.g., 125°–150° C., are more suitable with dibromoethane or diiodoethane as the alkylating agent whereas with dichloroethane as reactant, higher temperatures, e.g., 175° C. and up, are generally required. Generally, the use of the higher temperatures tends to be detrimental to obtaining the desired 4,4'-isomer. However, lower temperatures can be employed if iodine is used as promoter in the reaction. This is particularly advantageous when dichloroethane is the alkylating agent since it precludes the use of superatmospheric pressures in the process. When so used the iodine is introduced into the reactor in molecular form, either as iodine crystals or as a vapor; the iodide ion, I$^-$, is not generally effective in promoting the reaction. Amounts of iodine in the range from about 0.001 to about 1.0 mole per mole of dihaloethane are satisfactory for this purpose. Preferably, 0.01 to 0.05 mole per mole of dihaloethane is employed.

The 4,4'-dihydroxydiphenylethane can be readily recovered from the reaction mixture by conventional techniques. If the catalyst is present in solid form, it is removed by filtration. If the catalyst is in the dissolved state it is extracted or washed out with water. The catalyst-free reaction mixture is then distilled to strip out any unreacted dihaloethane and excess phenol. A fraction rich in the 4,4'-isomer can then be recovered from the remaining mixture by adding an amount by weight equal to said residue of a selective solvent such as dichloroethane, dibromoethane or chlorocyclohexane and cooling to effect crystallization. The crystalline fraction is separated by filtration and can be purified by continued recrystallization with an acetic acid-water mixture, a mixture of alcohols, dichloroethane or other suitable solvent to the 4,4'-isomer of the desired purity.

In order to increase yield of the desired product, the filtrate containing bisphenol-type oligomers and/or tars can be subjected to transalkylation and/or isomerization. This is effected by heating it at a temperature from about 150° to about 250° C. in contact with phenol and zinc bromide or zinc chloride and the corresponding hydrogen halide and then recovering the isomer from the resulting mixture.

In an alternative method, all the isomers can be recovered as a fraction from the stripped residue by treating the residue with acetone or other suitable solvent and then treating it with a decolorizing agent such as activated carbon to absorb the oligomers and/or tars and obtain a pale yellow solution from which the solvent can be evaporated. The 4,4'-isomer may be recovered from the mixture in substantially the same manner as described above. The residual isomer mixture can then be subjected to an isomerization step to increase the content of the 4,4'-isomer therein by heating it with phenol in contact with zinc bromide and treating with HBr or with zinc chloride in conjunction with HCl. Recovery of the isomer can then be effected by crystallization and re-crystallization to the desired purity.

The invention is illustrated in the following example which, however, is not to be construed as limiting it in any manner.

EXAMPLE

A series of runs was made in which phenol and 1,2-dibromoethane (DBE) were reacted using zinc oxide and zinc bromide separately and in combination as catalysts. The phenol was melted and 37.6 g (0.40 mole) was charged to a 100-cc, four-necked flask. The catalyst was added to the flask and a thermowell, sampling port, reflux condenser and dropping funnel were connected to it. The contents of the flask was heated to the reaction temperature of 150° C. while subjected to magnetic stirring. Then 0.1 mole of 1,2-dibromoethane (8.6 cc, 18.8 g) was added slowly over a period of about 15–30 minutes through the dropping funnel. The mixture was stirred at reaction temperature over a given period of time with the HBr off-gas being vented.

Samples were taken periodically and analyzed for dihydroxydiphenylethanes collectively by gas chromatographic means. Certain of these samples were subjected to acetylation by heating at 100° C. with an excess of acetic anhydride and the acetylated product was again analyzed by gas chromatographic means to determine the percentage (by wt) of the 4,4'-isomer present in the acetylated dihydroxydiphenylethanes of the reaction mixture. The conditions for the various runs and the results obtained are presented in the table below.

TABLE

| Run No. | Catalyst System (Mole/Mole DBE) | Dihydroxydiphenylethane Product (Area %) | | | | | | | Final Content 4,4'-Isomer (Wt %) |
| --- | --- | --- | --- | --- | --- | --- | --- | --- | --- |
| | | 0* Time | 30 Min | 1 Hr | 1¾ Hr | 2¼ Hr | 2¾ Hr | 4 Hr | |
| 1 | ZnO 0.4 | 0 | 0 | 0.2 | | 19.7 | | | 17.6 |
| 2 | 0.35ZnO/0.05ZnBr$_2$ | 0 | 13.3 | 17.4 | | | | | 15.3 |
| 3 | 0.2 ZnO/0.2 ZnBr$_2$ | 6.1 | 10.5 | 14.6 | 18.2 | | | | 15.4 |
| 4 | 0.05ZnO/0.35ZnBr$_2$ | 2.0 | 5.7 | 9.3 | | | 17.0 | | 13.6 |
| 5 | ZnBr$_2$ 0.4 | 0 | 2.5 | 5.1 | | | | 20.4 | 11.8 |

0* time is defined as time of completion of dibromoethane addition; other times are from end of dibromoethane addition

What is claimed is:

1. A process for the production of dihydroxydiphenylethanes which comprises alkylating phenol with 1,2-dibromoethane in at least the stoichiometric proportions of 2:1 in contact with a catalyst comprising preformed zinc oxide and preformed zinc bromide in molar proportions in the range from about 1:10 to 10:1 and at a temperature in the range from about 125° C. to about 225° C.

2. The process of claim 1 wherein the mole ratio of phenol to dibromoethane is in the range of from about 2:1 to about 4:1.

3. The process of claim 2 wherein the molar proportions of the zinc oxide and zinc bromide are in the range from about 1:1 to about 8:1 and the amount of catalyst employed is from about 0.001 to about 2 moles per mole of dibromoethane.

4. The process of claim 3 wherein the amount of catalyst employed is from about 0.01 to about 1.0 mole per mole of dibromoethane.

* * * * *